United States Patent [19]

Spako et al.

[11] Patent Number: 5,103,395
[45] Date of Patent: Apr. 7, 1992

[54] SYSTEM FOR REMOTE POSITIONING OF A RADIOACTIVE SOURCE INTO A PATIENT INCLUDING MEANS FOR PROTECTION AGAINST IMPROPER PATIENT EXPOSURE TO RADIATION

[76] Inventors: David W. Spako, 416 Park Ridge Dr., River Ridge, La. 70123; Michael Hayman, 1427 Eighth St., New Orleans, La. 70119; Arthur M. Zatarain, 401 Arlington Dr., Metairie, La. 70001

[21] Appl. No.: 569,522
[22] Filed: Aug. 20, 1990

Related U.S. Application Data

[63] Continuation of Ser. No. 255,044, Oct. 7, 1988, abandoned.

[51] Int. Cl.⁵ ............................................. G02F 5/02
[52] U.S. Cl. ................................................ 364/413.26
[58] Field of Search .................... 384/413.26; 414/1-8

[56] References Cited

U.S. PATENT DOCUMENTS

| | | | |
|---|---|---|---|
| 1,953,915 | 4/1934 | Burgett et al. | 219/8 |
| 2,904,272 | 9/1959 | Barrett | 242/54 |
| 3,664,517 | 5/1972 | Germond et al. | 414/1 |
| 3,669,093 | 6/1972 | Sauerwein et al. | 128/1.1 |
| 3,861,380 | 1/1975 | Chassagne et al. | 128/1.2 |
| 4,150,298 | 4/1979 | Brault et al. | 250/497 |
| 4,367,998 | 1/1983 | Causer | 414/1 |
| 4,631,415 | 12/1986 | Sauerwein et al. | 250/497.1 |
| 4,692,628 | 9/1987 | Sauerwein et al. | 250/497.1 |
| 4,733,653 | 3/1988 | Leung et al. | 128/1.2 |
| 4,756,655 | 7/1988 | Jameson | 414/7 |
| 4,837,734 | 6/1980 | Ichikawa et al. | 414/1 |
| 4,861,520 | 8/1989 | van't Hooft et al. | 252/644 |
| 4,881,937 | 11/1989 | van't Hooft et al. | 600/3 |
| 4,881,938 | 11/1989 | van't Hooft | 600/3 |
| 4,969,863 | 11/1990 | van't Hooft et al. | 600/3 |

FOREIGN PATENT DOCUMENTS 2092776 8/1982 United Kingdom.

OTHER PUBLICATIONS

Mick Radio-Nuclear Instruments Inc., 5 Gammamed ® IIi, System Dr. Sauerwein, "A Multi-Channel Remote Afterloading Device for Intracavitary, Interstitial and Intraluminal Radiation Therapy."
Nucletron, Micro Selectron LDR/MDR $^{192}$Ir $^{137}$Cs, p. 3.

Primary Examiner—Gary O. Hayes
Attorney, Agent, or Firm—Fitch, Even, Tabin & Flannery

[57] ABSTRACT

Remote controlled afterloader apparatus and method positions high activity radioactive sources through a catheter within a human body for treatment of cancerous tissue. The afterloader including an operating console and a remotely located wire driver. The wire driver includes active and dummy source wires and channels for the storage of such wires. Stepper motors precisely position the wires in response to computer control and data from wire position encoders. An emergency dc motor retraction system is provided for the active wire. A non-computerized cross-check interlock and emergency retraction system provides a high degree of safety against system malfunction. A turret is provided with safety locking and cross-checking systems to permit use of multiple catheters. The dummy wire is inserted into each catheter to verify catheter integrity prior to insertion of the active wire. Treatment profiles are conducted from the maximum extension position whereby only tension or retraction forces are used to position the active wire.

21 Claims, 9 Drawing Sheets

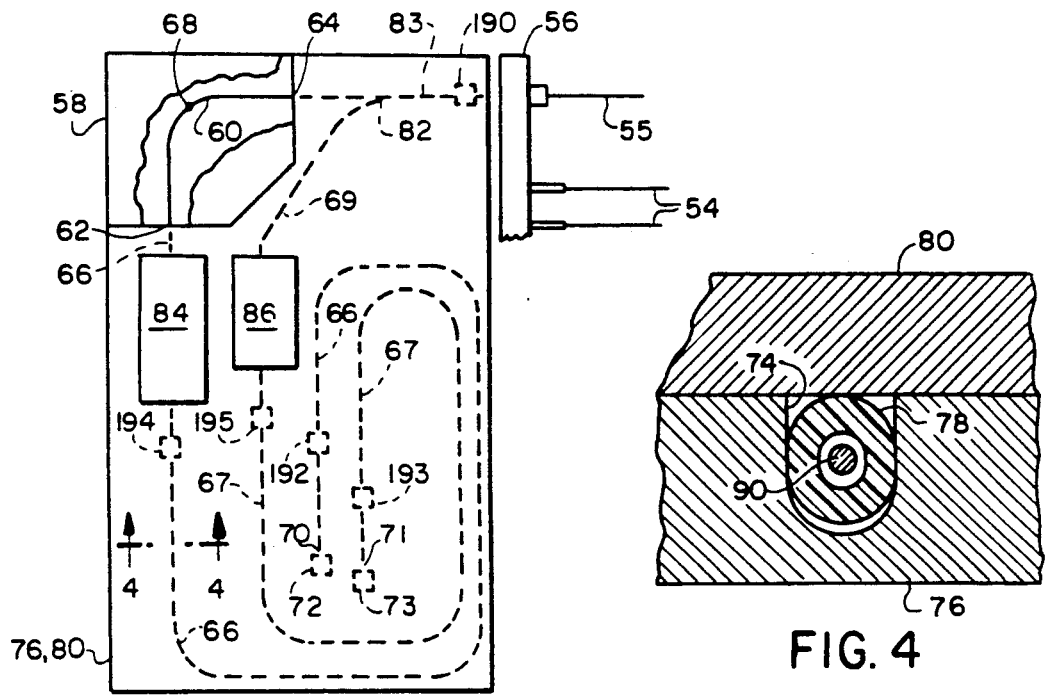
FIG. 3
FIG. 4
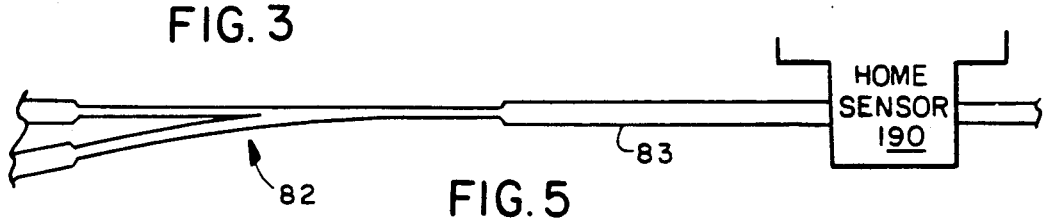
FIG. 5
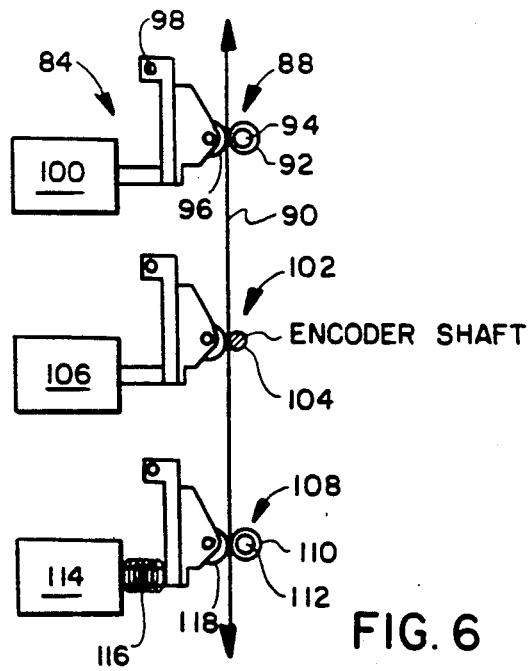
FIG. 6

SYSTEM FOR REMOTE POSITIONING OF A RADIOACTIVE SOURCE INTO A PATIENT INCLUDING MEANS FOR PROTECTION AGAINST IMPROPER PATIENT EXPOSURE TO RADIATION

RELATED APPLICATIONS

This is a continuation of U.S. patent application Ser. No. 07/255,044, filed Oct. 7, 1988 now abandoned.

The present invention relates generally to methods and apparatus for the handling of high activity radioactive sources in the treatment of cancerous tissue.

The use of radioactive material in the treatment of cancer is well known in the medical field. Treatment techniques, however, vary dramatically depending upon the location of the cancerous tissue and the activity level of the radioactive source used in treatment.

One common treatment procedure involves the use of relatively low activity radioactive seeds. Due to their low activity levels, typically about 1 millicurie/centimeter, these seeds remain resident in, or adjacent to, the tissue undergoing treatment for extended periods of time, for example, several days. As a consequence, the seeds are surgically implanted, thereby allowing the patient to continue normal activities during the resident treatment period.

One of the principal advantages of such low activity treatment procedures is the ease of handling of the radioactive sources or seeds, themselves. While ordinarily stored in radioactive "safes" when not in-use, these low activity seeds may otherwise be handled freely by doctors and support personnel during implantation and removal. The disadvantages of this treatment technique, however, are long residency times and the requirement for surgical implantation and removal, the latter with its attendant trauma to adjacent normal tissue.

At the other end of the treatment spectrum are the high activity radioactive treatment procedures. These procedures, which typically employ radioactive sources in the range of 10 curies, present significant handling and treatment challenges. On the other hand, a significant offsetting advantage of such a treatment regime is its extreme speed. A complete treatment session can be completed in only a few minutes. The patient carries no radioactive implants within him from the treatment center.

A ten curie source cannot be openly handled or exposed to treatment facility doctors and personnel. Even relatively short exposures may result in radiation burns. As a consequence, high activity radiation therapy must be conducted remotely, with the radioactive source being removed from a shielded container or "safe" to the point of treatment, and thereafter returned, all by mechanical means.

It will be appreciated that apparatus for positioning high activity sources must be of uncommon integrity, accuracy, and reliability. It must have safeties, back-ups, and means for assuring that, in no event, can a source be lost, left behind, misplaced or, simply fail to retract into the safe, even for relatively short durations of time. The possibility for irreversible damage to normal tissue, in the time required for manual intervention upon system failure, is simply too great. As set forth in more detail below, the present invention describes a remote source afterloader having a high degree of reliability and emergency back-up protection against system failure or loss of control.

The mechanical placement of high activity sources requires precise and accurate positioning both to assure proper dosage levels to cancerous tissue as well as to minimize damage to adjacent normal tissue. By reason of the intense radiation associated with high activity sources, real-time, hand-guided source placement by the treating physician is precluded. The source, therefore, is inserted through a tube, needle, or catheter previously surgically positioned in the patient.

The use of catheters, although less invasive than the open surgical implantation of seeds, nevertheless traumatizes tissue along its path of insertion. In delicate tissue regions, for example, in the brain, such trauma must be kept to an absolute minimum. Known prior art high activity sources are affixed to the end of delivery wire of substantial diameter, typically in excess of 1 millimeter. As a consequence, the delivery wire and source must be inserted through correspondingly large tubes, needles or catheters.

Recent developments in high activity source manufacture have resulted in the availability of an ultra-thin iridium source of less than 0.5 millimeters in diameter which, in turn, permits the use of significantly narrower catheters. This source is disclosed in U.S. application Ser. No. 228,400, filed Aug. 4, 1988. In its preferred arrangement, the source comprises a 1 centimeter active region of relatively pure iridium positioned 1 millimeter from the end of 2.1 meter platinum delivery wire. Such ultra-thin radiation sources, in combination with the present remote afterloader, now permit radiation treatment in, or proximate to, delicate tissue areas at heretofore unrealizably low trauma levels.

The present invention, therefore, is directed to a remote afterloader having the capability of properly advancing and positioning this new ultra-thin wire. It will be appreciated that these new ultra-thin source wires do not exhibit the same strength characteristics, particularly in buckling, as the more massive prior art wires. Thus, existing remote afterloader apparatus, which were developed for these heavier gauge wires, have proved unsuitable.

One such prior art device, for example, uses a drum onto which the delivery wire is wound, thereby retracting the wire from the catheter and patient. Extension of the wire, however, requires a smooth cylindrical shroud oriented around the outside of the drum against which the wire coil expands as the drum is rotated in the uncoiling direction. Upon contacting the shroud the wire is urged through a narrow opening or slit therein, then, into the catheter for delivery to a tumor site. This arrangement is wholly unsatisfactory for ultra-thin delivery wires. These wires simply do not have sufficient buckling integrity to permit the relatively unguided movement central to drum/shroud operation.

The present afterloader incorporates a dual-capstan drive arrangement in which one capstan positively feeds the delivery wire while the second capstan precisely meters wire movement. Importantly, the path of the delivery wire within the afterloader itself is tightly constrained, in both directions from the capstan drive assembly, thereby precluding buckling of the wire. More specifically, a low friction channel or tube having sufficient length to store all but the active tip region of the delivery wire is provided below the capstan drive. This channel is of minimum cross-section thereby precluding wire bending or deformation. Above the capstan drive, the delivery wire, including the iridium source, feeds into a narrow tubular structure defining the interior of a radioactive safe, then through a narrow outlet channel to a multiple catheter turret assembly. In this manner, there are no open regions within the remote driver apparatus which might permit wire buckling during either extension or retraction.

The above wire containment structure serves another extremely important safety function. It is imperative to establish that the highly radioactive iridium source portion of the delivery wire is, in fact, safely retracted and stowed within the safe. Failure to properly identify a non-stowed condition could result in a severe overdose to the patient and to personnel who enter the treatment environment under the mistaken belief that the source has been properly retracted.

Prior art systems provide no positive means for identifying proper source stowage. Indeed, these systems provide no indication whatsover of an "overstowage" condition, that is, where the retraction mechanism does not disengage upon source stowage. Under such conditions, the active element of the wire can be withdrawn from the bottom of the safe, thereby leaving a hot source exposed within the remote wire driver equipment chassis. This condition represents a serious safety hazard to anyone entering the treatment room.

The present afterloader, by contrast, employs redundant systems to verify proper source stowage. One of these systems, importantly, provides unfailing and absolute protection against wire over-retraction. Specifically, the end of the narrow wire channel is obstructed to preclude further wire travel thereby defining a maximum wire retraction limit. Should the retraction drive capstan continue to operate after full wire retraction, due to some circuit or controller malfunction, further inward movement of the delivery wire necessarily ceases. The capstan cannot force the wire further into the channel; rather, the capstan merely and harmlessly slips. This position corresponds to proper stowage of the active region within the lead safe.

Abutting engagement between the delivery wire and channel end does not, however, insure that the active region of the wire has been safely stowed. For example, were the delivery wire to sever, the inactive end could properly seat against the channel end while the active region remains outside the safe, possibly still within the patient.

The present invention provides absolute protection against such false indications of wire stowage. In this connection, the wire guide and storage channels additionally serve to facilitate highly accurate wire length measurement. Specifically, a pair of optical wire sensors is precisely spaced along each channel slightly less than the length of the respective delivery wire such that the sensors can register the simultaneous presence of both wire ends of the respective delivery wire, but only when the wire is of full undamaged length. Delivery wire length is checked upon initial wire extension, as well as upon retraction and stowage.

In addition to the absolute and unerring determination of active element stowage, it is critical that the position of the active source be known at all times with high accuracy and reliability. Improper positioning not only endangers normal tissue, but may result in the failure to treat cancerous tissue. The control circuitry of the present invention provides a high degree of operational cross-checking with automatic wire retraction occurring upon cross-check failure.

Wire delivery and position determination is predicated upon the previously noted dual-capstan arrangement in which a computer controlled stepper motor drives the first capstan and a position encoder, also connected to the computer, is driven by the second capstan. Each computer controlled step of the drive motor produces a precisely known axial movement of the delivery wire and, in turn, a corresponding and known response from the encoder. The output from the encoder is compared against the stepper motor commands, both on an incremental per step basis and on an overall basis. At the incremental level, the absence of proper encoder signals following one or more steps signifies a wire jam, and further wire delivery is terminated.

The computer further cross-checks the overall number of encoder output pulses actually received against the number of expected pulses based on the number of stepper motor steps commanded. A predetermined, but small, discrepancy is permitted between the computed and actual number of drive motor steps to account for capstan slippage. However, should encoder outputs cease entirely following stepper motor actuations or should the overall number of encoder outputs not fall within the predetermined limits, it is assumed that a delivery wire jam or obstruction has been encountered. In any event, the precise positioning of the wire cannot be assured under such conditions, and, therefore, the wire will be withdrawn.

The delivery of high activity radioactive sources requires afterloader apparatus comprising two distinct and separately located subsystems. First, an operator console is provided. This console is located in a room separate from the radioactive source thereby avoiding exposure of treatment personnel to radioactivity while the source is extended from its safe. The second subsystem is the mechanical source storage and delivery apparatus which physically feeds, under computer control, the active source from the safe to precise locations within the patient, and for precise time intervals.

It is a critical feature and objective of the present invention to position the source accurately within a patient and then to withdraw the source, both steps to be performed with a high degree of certainty that the source is actually where it is supposed to be. As set forth above, the described apparatus provides the requisite accuracy as long as the computer control is properly functioning.

Computers, however, occasionally malfunction. Therefore, the present afterloader provides for monitoring of proper computer function and, in the event of computer or other malfunction, for the automatic emergency retraction of the radioactive source.

The emergency retraction system functions at the most basic circuit level, thereby virtually eliminating the possibility of emergency backup system failure. In the first instance, the emergency system operates from a constantly recharging backup battery source. This backup source is constantly monitored by the computer which, in turn, signals a backup power failure, simultaneously blocking extension of the active source wire until proper backup system operation has been restored.

The emergency retraction system requires no computer control. It does not utilize the normal capstan drive stepper motors, instead, a separate dc motor driven capstan is provided. Upon primary system failure, power is switched to this motor, thereby forcing full wire retraction. This emergency motor continues to operate until the inactive end of the delivery wire engages a switch positioned at the end of the wire stowage channel. As noted above, the delivery wire cannot be over-retracted should this switch fail. As the wire cannot be retracted beyond the channel end, the emergency retraction capstan merely slips.

Watchdog timers are provided within the remote wire driver subsystem to monitor computer control signals. In the event that valid computer control signals are not received within a preset interval, computer failure is assumed, and the automatic emergency retraction sequence is engaged.

Additional operational and apparatus subsystems are included to further assure proper overall system operation. One such subsystem is a wire delivery pretest subsystem. This subsystem assures proper active wire extension by first checking the placement and integrity of each catheter. This test is performed by extending a dummy wire through each catheter tracing the treatment profile intended for the active wire.

The dummy wire drive apparatus is substantially identical to that previously described for the active wire, although no emergency retraction system is incorporated. Thus, undue slippage or jamming of the dummy wire, or a failure to retract fully, signals a fault condition which precludes active wire extension. Importantly, this fault condition is registered, not merely by the computer, but at the remote wire driver apparatus itself, whereby extension of the active wire will be precluded even though the computer may have failed to register the fault condition.

A similar fault detection/protection arrangement is provided in connection with the optional multiple catheter turret. In this connection, the present invention may advantageously incorporate a turret arrangement permitting connection of up to ten separate catheters. In this manner, multiple catheters may be positioned within a patient to facilitate the more complete treatment of the cancerous tissue area in one radiation application session. Under computer control each catheter is accessed, in turn, and the appropriate preprogrammed treatment regime implemented. This regime includes the above described catheter pretesting by first extending the dummy wire.

It is imperative that no attempt be made to extend the dummy and active wires unless the turret is properly indexed at a valid catheter location having a catheter inserted therein. Consequently, detectors are provided to signal both the existence of the catheter and the proper indexing of the turret. Again, a turret or catheter fault condition is registered, not merely by the computer, but by the remote wire driver apparatus thereby assuring proper fault-induced inaction regardless of computer operation.

From the foregoing it will be apparent that the present invention provides for the control of remotely located radioactive source wire driver equipment. More particularly, apparatus for precisely positioning ultra-thin sources and delivery wires is provided such that the wire may be extended from, and returned to, a safe without likelihood of wire buckling. The proper stowage of the active source within the safe is determined with high reliability and the active source is absolutely precluded from over-retraction. A low friction delivery wire channel serves to guide the wire, prevent buckling, preclude over-retraction, and aid in the detection of wire breaks. Emergency backup active wire retraction is provided in the event of computer or other malfunction. Dummy wire testing of all catheters is performed. A multiple catheter selection turret may be provided. Cross-fault detection is employed to preclude active and dummy wire extensions unless the other wire is properly retracted and parked and unless the turret is properly indexed to a valid catheter position. Other features of the invention are disclosed in the following figures, written specification and claims.

BRIEF DESCRIPTION OF THE DRAWINGS

FIG. 3 is a left side elevation view of the remote wire driver of FIG. 1 with a portion broken away illustrating the placement of the active and dummy wire storage and guide channels and of wire drive assemblies and wire position detectors;

FIG. 4 is a sectional view of the driver taken along line 4—4 of FIG. 3 illustrating details of the wire storage and guide channels;

FIG. 5 is a left side elevation view of the Y-shaped region of the driver defining the junction between the active and dummy channels;

FIG. 6 is a left side elevation view of the active wire drive and emergency retraction system;

DESCRIPTION OF THE PREFERRED EMBODIMENT

Figure 1:
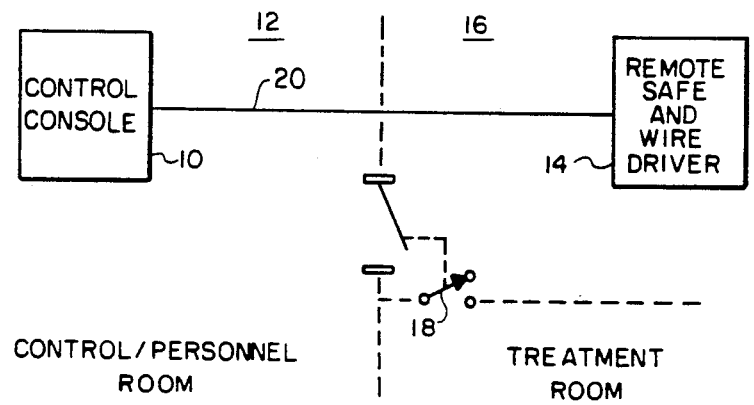
FIG. 1 is a block representation of the present wire afterloader illustrating the placement of the remote safe and wire driver in a treatment room separate from the control console.

The remote afterloader of the present invention, as shown in its most general form in FIG. 1, includes a computerized control console 10 located in a control room 12 and a remote safe and delivery wire driver 14 located in a treatment room 16. Federal regulations require, in view of the high radiation levels associated with high activity sources, that patients undergoing treatment be placed in shielded treatment rooms isolated from the attending physicians and other personnel. Thus, the treatment room 16 complies with appropriate federal regulations for shielding and, further, is provided with an entrance door interlock 18 to automatically retract, as discussed in more detail below, the active source upon entrance of non-patient personnel into the treatment room. A data and control bus 20 interconnects the console 10 with the remote driver 14.

Figure 2:
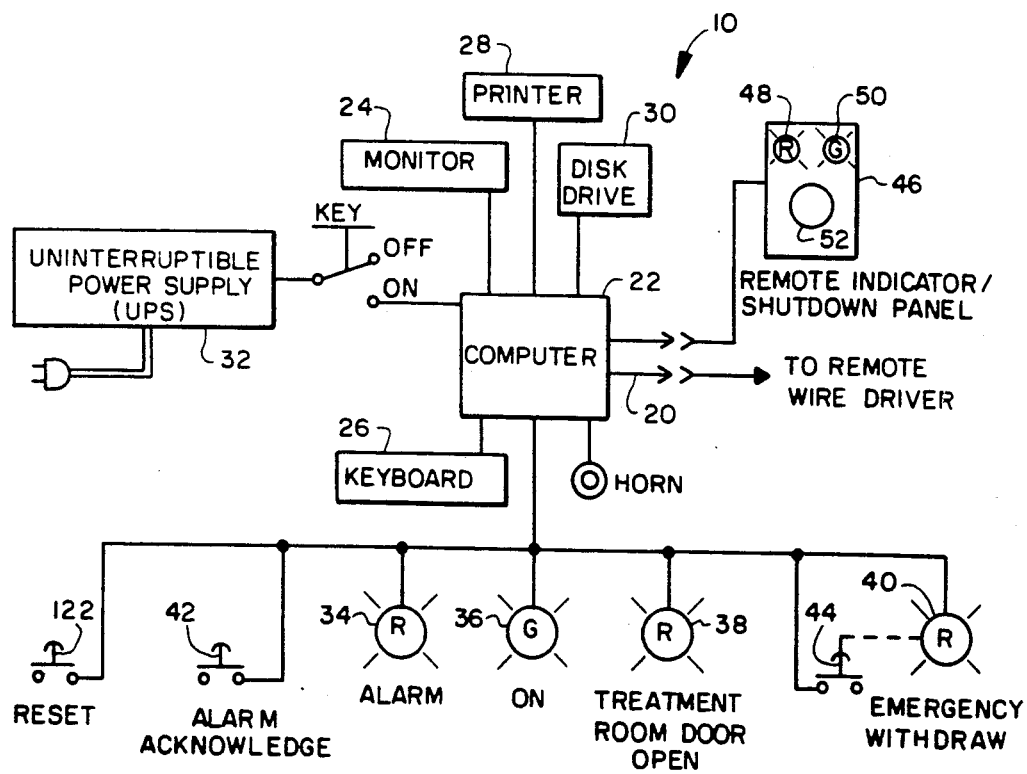
FIG. 2 is a functional block diagram of the control console of FIG. 1.

FIG. 2 is a block illustration of the control console 10 which includes a computer 22 of conventional availability incorporating a color monitor 24, a keyboard 26, a printer 28 and floppy disk drive 30. More specifically, the computer is of the well-known 80386 processor variety and includes an additional 40 MByte hard drive. A uninterruptible power supply 32 is provided to protect against losses of power during on-going treatment sequences.

Also pictured are various annunciators and specific control function input buttons. Alarm 34, 'on' 36, treatment room door open 38, and emergency retract 40 annunciators as well as alarm acknowledge 42, emergency withdraw 44, and reset 122 buttons are provided on the control console itself. A remote shutdown/annunciator box 46 is provided at the treatment room door. This box includes treatment in progress 48 and ready 50 annunciator and an emergency stop or retract button 52.

FIG. 3 illustrates various structural features of the remote driver 14. A plurality of tubes or catheters 54 are shown connected to a catheter selector turret 56. The uppermost catheter 55 is shown in the active position. It is through this catheter that delivery wires are extended.

There are two delivery wires, one active and one dummy. Each is fabricated of platinum and is of approximately 0.45 millimeters in diameter. In the preferred arrangement, the active delivery wire has an overall length of 2.1 meters and contains a 10 millimeter long seed of activated iridium spaced 1 millimeter from the forward end thereof. The dummy wire is 1.8 meters in length and does not contain an iridium seed.

The iridium seed of the active wire is typically irradiated to an activity level of 10 curies and, therefore, represents a potentially dangerous source of radiation that must be properly stored when not in use. A lead shielded safe 58 is provided for this purpose. Referring still to FIG. 3, the safe 58 is provided with a 90 degree radius bronze tube 60 of sufficient diameter to pass the 0.45 mm active wire source. The tube defines a lower inlet 62 into which the active wire feeds from its guide and storage channel, discussed in more detail hereinafter, and an outlet 64 from which the active wire source is extended, thereafter, through the turret 56 and into the active catheter 55.

The active wire guide channel is depicted by the dotted line 66. The dummy guide channel is shown by dotted line 67. The overall length of the active channel 66 is selected such that the 10 mm active portion of the wire, i.e. the iridium seed, will be centered in the safe 58 at its midpoint 68 when the opposed rearward wire end abuts a park switch 72 positioned at end 70 of the active channel. In similar fashion, the overall length of dummy guide channel 67 is selected such that the forward end of the dummy wire will be retracted to a non-interfering position 69 when the opposed rearward end thereof abuts a dummy park switch 73 at channel end 71. The channels are broadly radius, preferably to about 50 mm, to minimize wire friction therewith.

The cross section of one of the active and dummy guide channels 66,67 is shown in FIG. 4. Both channels are formed, for example, by milling recesses 74 in the surface of a path plate 76. These recesses are dimensioned to receive and securely retain a teflon tube 78 having an inside diameter of approximately 0.8 mm. The tubes 78 may additionally be glued within the recesses 74. A cover plate 80 is bolted to the path plate 76 to protect the tubes 78 and assure that they remain in position.

By reason of the above described construction, it will be seen that the iridium seed cannot be drawn further into the safe than the midpoint 68 nor, therefore, can it be over-retracted and withdrawn entirely from the safe through the inlet 62. There simply is no place for the wire to go or buckle once it is fully parked with its rearward inactive end seated against the switch 72.

It should be noted that other channel constructions are contemplated by the present invention. Any construction providing for the low friction stowage of a predetermined length of delivery wire, and without substantial openings or volumes into which the wire might buckle, should be satisfactory.

Referring to FIGS. 3 and 5, the respective active and dummy wire channels merge in a "Y" or wishbone channel section 82, thereafter forming a single output channel 83 operatively interconnected with the turret 56. Unlike the remainder of the channel sections, the wishbone portion does not incorporate a tube member within its recess. Instead, the recess is milled to the ultimate channel working dimension through which the respective active and dummy wires pass directly. The preferred recess depth is 0.5 mm with a 0.5 mm radius therebelow.

The active wire drive and emergency retraction system 84 is shown in FIG. 6. The dummy wire drive system 86 is identical, except that the emergency retract motor is omitted. The uppermost capstan defines the stepper motor wire drive assembly 88. This assembly, under computer stepper control, moves the active wire 90 (along the previously identified path 66) in both the extension (upward) and retraction directions. As described in more detail below, the active wire is extended to the maximum treatment position then, as required by the prescribed treatment profile, retracted in precisely timed intervals of predetermined distance until the entire treatment cycle for the given catheter has been completed. The stepper motor wire drive assembly 88 is not ordinarily used for emergency retraction.

Figure 18:
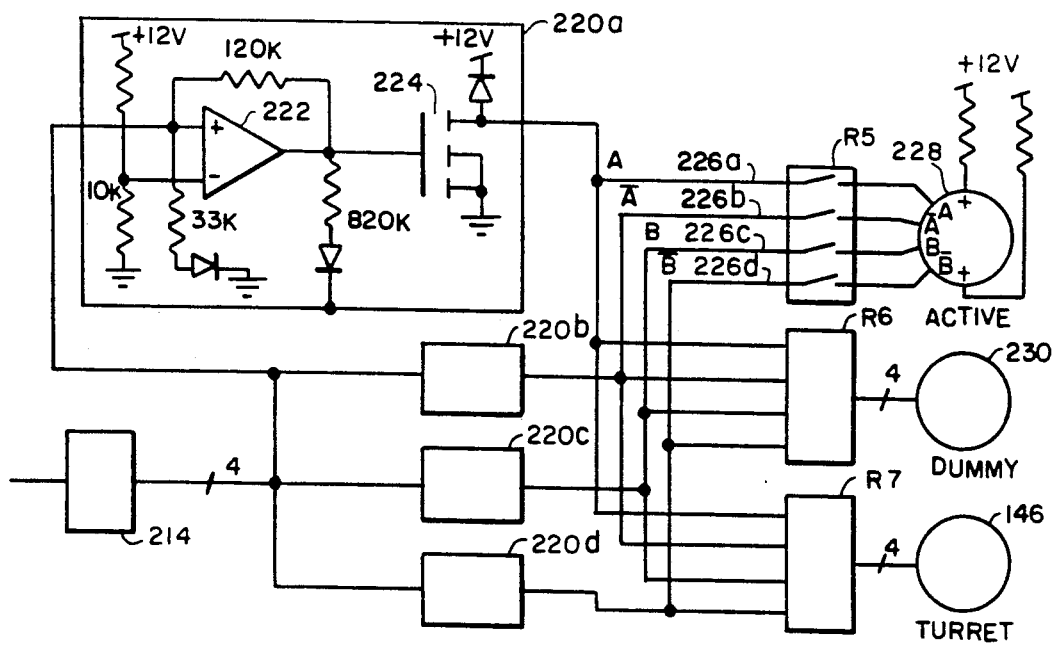
FIG. 18 is a schematic and block representation of the remote wire driver stepper motor driver system.

As shown in FIG. 6, the stepper drive assembly 88 includes a rubber sleeve 92 fitted onto the steel shaft 94 of the stepper drive motor 228 (FIG. 18). This rubber sleeved shaft 92, 94 comprises the drive assembly capstan. A rubber pinch roller 96 is pivotally mounted at a pivot 98 and is urged against the capstan by pusher-type solenoid 100. Alternatively, a threaded screw adjustment (not shown) may be substituted for the solenoid to apply the requisite pinch roller pressure.

Below the drive capstan is the encoder drive assembly 102. It is substantially identical to the above described wire drive assembly except that an encoder 238 (encoder shaft or capstan 104 is shown) is substituted for the stepper drive motor 228. Operation of this capstan is, of course, in the opposite sense, that is, with the active wire 90 driving the encoder capstan rather than being driven thereby. Again, a screw adjustment may be substituted for the solenoid pinch roller actuator 106 illustrated.

The lowest capstan, used only in connection with the active wire drive and retract system 84, defines the emergency retract assembly 108. This assembly differs from the stepper motor drive assembly in two important aspects. First, the capstan, comprised of a rubber sleeved 110 motor shaft 112 is driven from a conventional, non-stepper type dc motor. Second, the pinch roller solenoid 114 is of the "pull" type and includes a spring 116 which biases a pinch roller 118 against the capstan. Solenoid power is required to retract the pinch roller thereby disengaging the emergency retract capstan. Thus, in the event of a computer failure or other system loss of control, power is dropped to emergency retraction solenoid 114, thereby automatically engaging the emergency retraction capstan, while emergency power is simultaneously applied to an emergency retraction motor. As this is a conventional dc motor, no special control or stepping instructions are required. Emergency retraction may be effected even though other portions of the afterloader system, including the computer 22, are inoperative.

Figure 7:
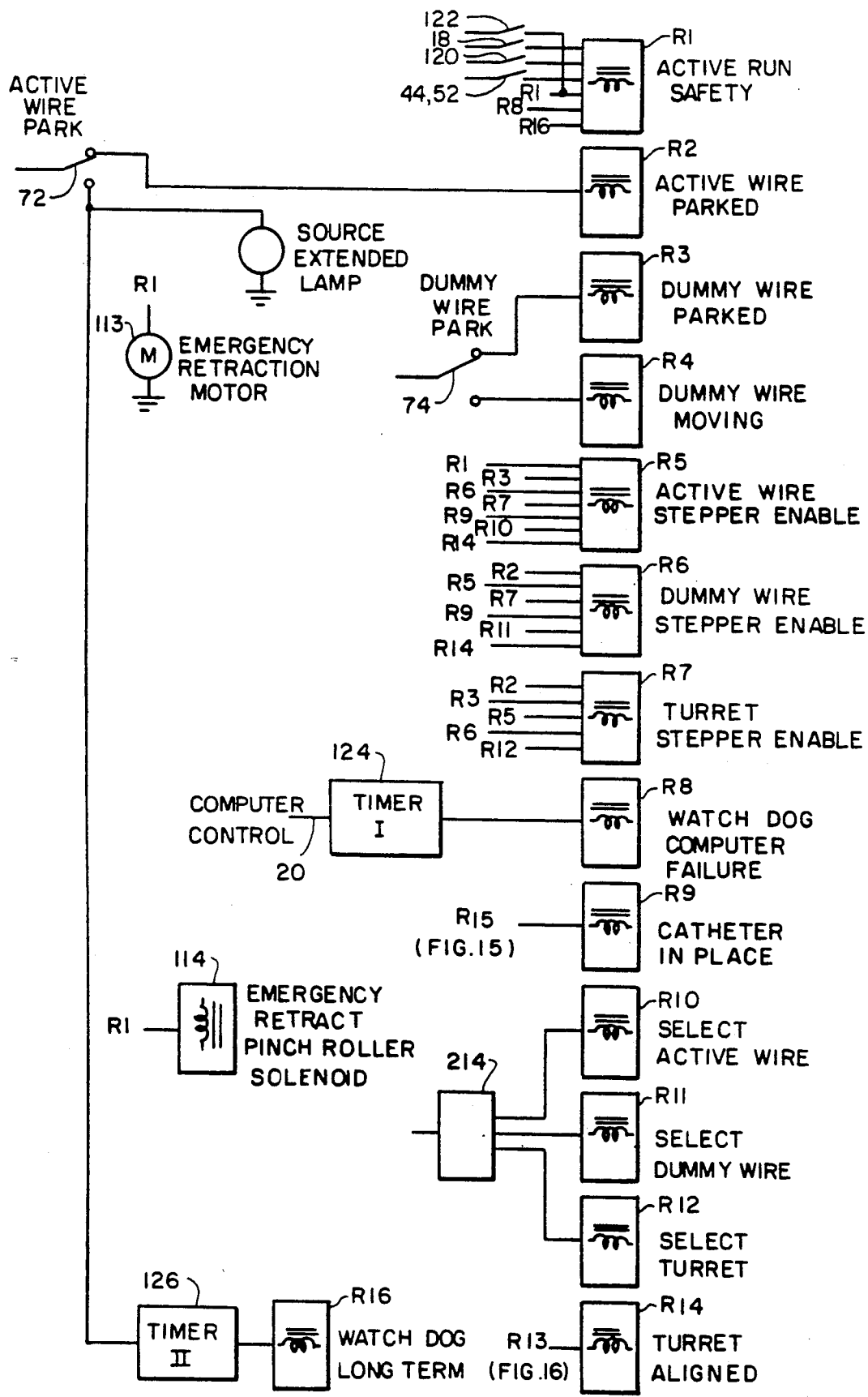
FIG. 7 is a functional block diagram of the cross-check interlock and emergency backup system of the present invention.

Operation of the emergency retraction and the other failsafe and interlock subsystems is best understood by reference to FIG. 7. The circuitry of FIG. 7 is physically located within the remote delivery wire driver apparatus 14 such that it can perform its emergency and interlock overseeing functions without concern for the integrity of the computer console 10 or the bus 20 interconnecting the remote wire driver and console. A review of FIG. 7 reveals that substantially all crucial safety interlocking functions are performed by combinations of simple switch and relay functions and including two integrated circuit 'watch dog' timers.

Relays R1-R7, R9, and R14 are 12 volt dc relays of conventional design which are energized from a 12 volt power supply bus upon satisfying their respective input requirements. More specifically, the 12 v power required to actuate each relay is applied to that relay through the series combination of switch and relay output contacts shown in FIG. 7. Relay operation, therefore, requires that all of the input conditions be met.

Run safety relay R1 is the heart of the emergency shut-down system. Upon the automatic detection of any system abnormality or difficulty, or upon the manual intervention by a system operator through the actuation of an emergency button, the relay R1 immediately deenergizes and remains deenergized until the cause of the problem has been corrected and the operator resets the system through switch 122 (FIG. 2).

The relay R1 is directly interconnected with both the emergency retraction dc motor 113 and to the emergency retract capstan solenoid 114 thereby instantly commencing the emergency retraction cycle upon relay deactivation. Power, from the emergency backup battery if necessary, is applied to the emergency retraction motor and simultaneously removed from the retraction capstan solenoid.

The emergency retraction cycle continues until the active wire 90 is fully retracted, as determined by wire engagement with the park switch 72 (FIG. 3). As previously noted, the active wire cannot be over-retracted even upon the failure of the emergency retraction motor to shut down. Once fully parked, any attempt to force the active wire further into the guide channel 66 merely results in slippage of the offending capstan drive.

Relay R1 monitors, and is energized, when the mandatory conditions for the continued extension of the active delivery wire have been met. These conditions include closure of the treatment room door interlock 18, the non-actuation of any of the console 44, door 52, or remote 120 emergency stop buttons, as well as proper operation of the watch dog timers, discussed below. Power to the run safety relay R1 is additionally routed through a set of normally open contacts of the relay R1, itself. Consequently, actuation of this relay, even if all of the above noted conditions have been satisfied, requires the momentary depressing of a reset switch 122.

The first of the watch dog timers, timer 124, monitors the activity on one line of the computer control/data bus 20. The computer outputs a periodic signal on this line every few milliseconds, but only when the computer hardware and software are functioning properly. If this signal is lost for more than about 600 milliseconds, the timer 124 deactivates the relay R8 which, in turn, releases the relay R1.

The second watch dog timer 126 commences timing whenever the active wire is extended. A maximum time of about 23 minutes is allotted for active wire extension. This time limit exceeds the duration of the longest treatment profile anticipated. Failure of the active wire to return to the parked position at least once every 23 minutes indicates a problem necessitating emergency active wire retraction.

For the purposes of the watchdog timer oversight, the park switch 72 signals the full retraction or parking of the active wire. In the absence of the required park signal within the predetermined time limit, the timer 126 deactivates relay 16, in turn releasing relay R1.

It will be appreciated that the above described run safety relay R1 system provides a highly reliable means for periodically forcing the immediate retraction of the active wire in the event of computer or other failure. Importantly, this system is self-contained on the remote driver 14 chassis; is of simple design thereby minimizing likelihood of failure; and incorporates backup power to further eliminate the possibility of emergency retraction failure.

The emergency retraction system is, however, but one of several important afterloader cross-check and interlock subsystems which function to minimize or preclude the possibility of improper system operation. Thus, the computer controlled movement of the turret and wires, either active or dummy, requires confirmation by the non-computerized cross-check and interlock systems of FIG. 7.

Three stepper motor enabling relays R5, R6 and R7, are provided, respectively, for the active wire, the dummy wire, and the turret. Until the corresponding relay has been energized, the computer controlled movement of the selected function is inhibited. Each of these enabling relays is interlocked to the other relays and to other functions considered critical for proper stepper motor operation.

Thus, active wire stepper motor relay R5 is energized only when all of the conditions required for the extension of the active wire have been met. Several important interlock conditions must be met for computer controlled movement of the active wire.

First, the above discussed emergency run safety relay R1 must be energized. Computer controlled movement of the active wire is, in short, incompatible with the emergency retraction function, and, therefore, active stepper motor operation is inhibited during the emergency retraction cycle.

Also required for active wire stepper motor operation are dummy wire parked (R3) and dummy stepper motor not enabled (R6), turret aligned (R14) and turret stepper motor not enabled (R7), catheter connected (R9), and computer commanded selection of the active wire (R10).

It is manifest that the dummy and active wires cannot simultaneously occupy the same catheter and therefore cannot be simultaneously extended. Consequently, any indication that the dummy wire is enabled for movement, or not parked, requires disabling of the active wire stepper motor. The dummy wire parked condition is signaled by the relay R4 activated, in turn, by the park switch 74.

Similarly, a misaligned turret, or a turret enabled for movement, is incompatible with active wire extension due to possible jamming of the active wire at the turret interface. Finally, the active wire must not be extended unless a catheter, through which the wire will travel, is properly interconnected. Thus, extension is prohibited in the absence of a proper catheter-in-place indication. These last requirements relating to the turret and catheter apply equally to the extension of the dummy wire and, consequently, it will be noted that these same enabling function relays, R7, R9 and R14, also define inputs to the dummy wire stepper motor enabling relay R6. Operation of the catheter-in-place and turret aligned relays R9 and R14 are described below.

Enablement of the dummy wire stepper motor relay R6 requires, in addition to meeting the above noted turret and catheter conditions, a parked active wire (R2), no indication that the active wire stepper motor is enabled (R5), and computer selection of the dummy wire (R11). Turret-stepper enable relay R7 requires parked and non-enabled active and dummy wires (R2,R3,R5,R6) as well as computer selection of the turret stepper motor relay R12.

From the foregoing, it is clear that computer commands which are inconsistent with existing remote driver 14 status will be ignored by the safety interlock systems thereby precluding the possibility of wire jamming which could, in turn, damage the afterloader and, importantly, could compromise proper operation of the emergency retraction system.

Figure 17:
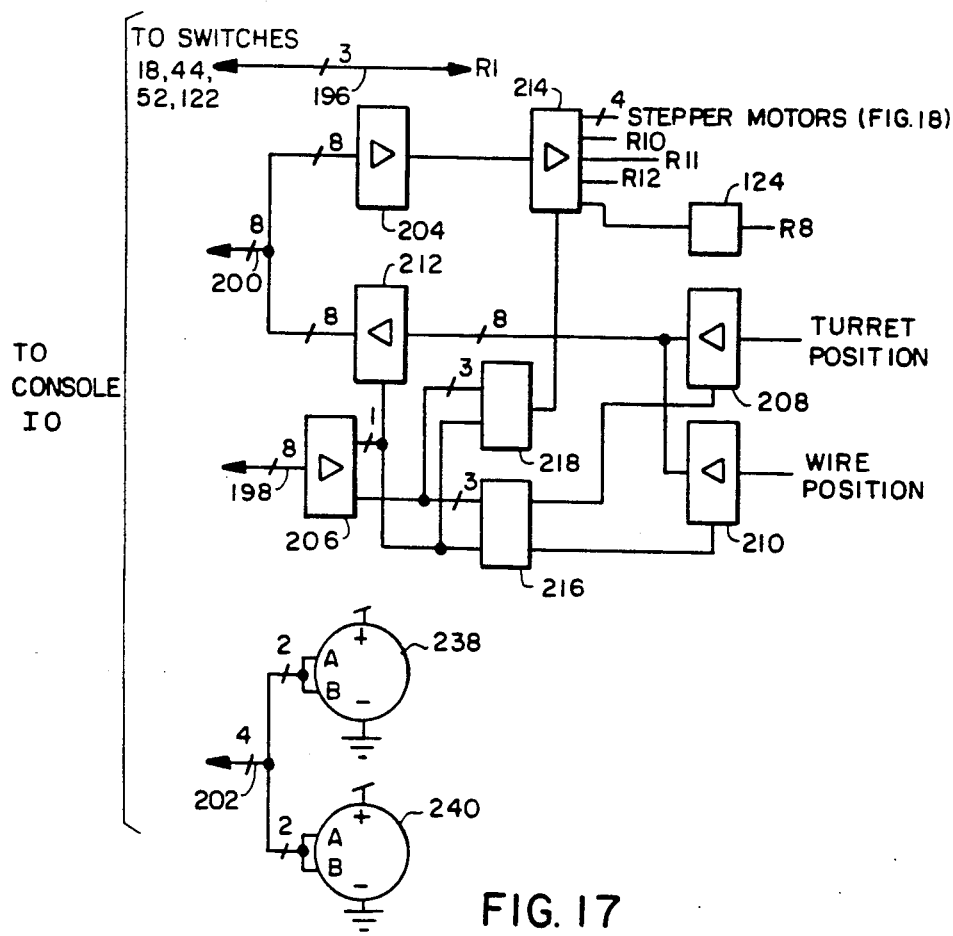
FIG. 17 is a block representation of the remote wire driver computer interface logic.

Relays R8, R9-12, R13, and R15 are driven directly from integrated circuit logic sources and, therefore, typically operate at lower voltages, for example 5 volts. The watchdog timers 124 and 126, for example, directly actuate respective relays R8 and R16. Similarly, active and dummy wire select and turret select relays R10-12 are each energized from a corresponding output of buffer/latch 214 (FIG. 17). Finally, the 12 v catheter-in-place and turret-aligned relays R9 and R12 are themselves actuated by logic-driven 5 v relays R15 and R13, respectively.

Figure 16:
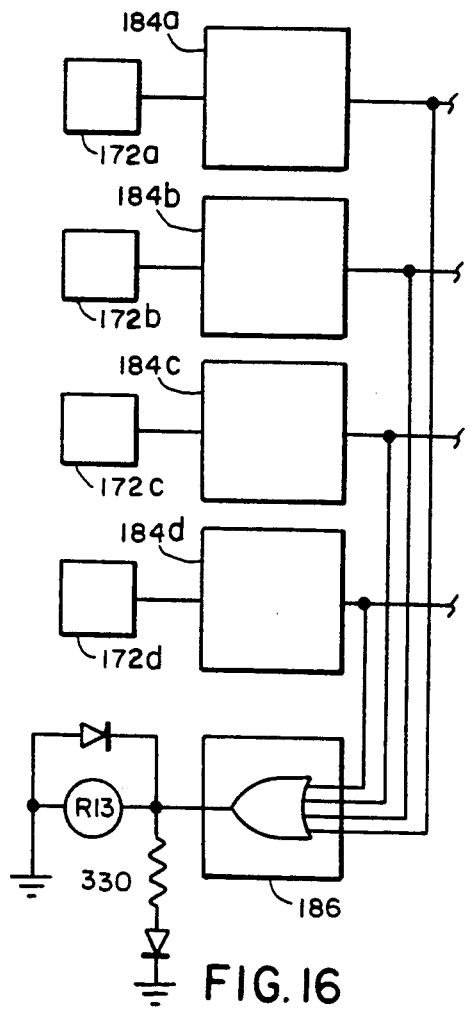
FIG. 16 is a block representation of the turret-position and turret-aligned detection system.

The catheter selector turret is shown in FIGS. 8-14. The catheter-in-place circuitry which activates the previously noted relays R15 and R9 is illustrated in FIG. 15. FIG. 16 depicts the turret indexed and aligned circuitry which functions to uniquely identify the catheter selected and to provide the requisite turret-aligned signal to relays R13 and R14.

Figure 8:
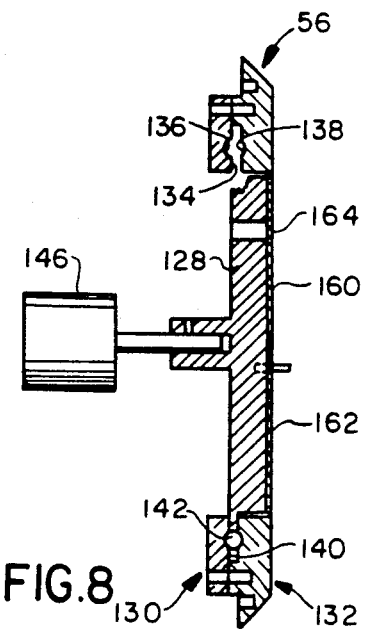
FIG. 8 is sectional view taken along line 8—8 of FIG. 13 of the catheter select turret assembly of the present invention.
Figure 13:
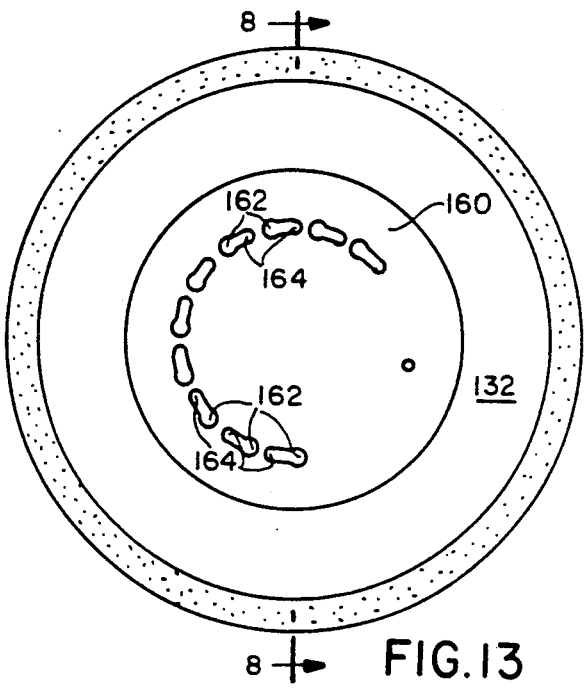
FIG. 13 is a front elevation view of the catheter select turret assembly showing the catheter locking plate.
Figure 9:
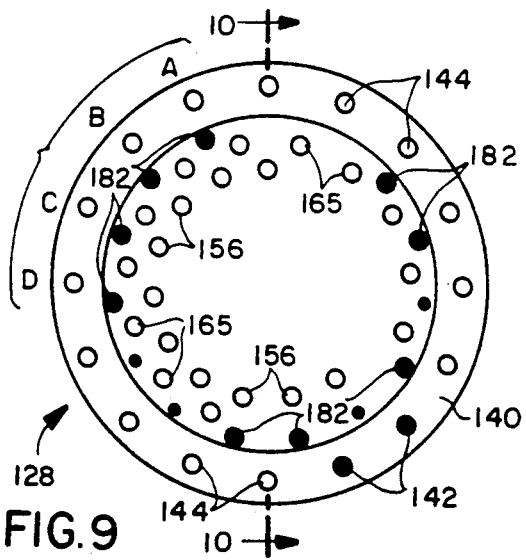
FIG. 9 is a rear elevation view of the rotating turret of the turret assembly.

Referring to FIGS. 8 and 9, the turret assembly 56 comprises a turret 128 retained for rotating movement between inner and outer race members 130 and 132, respectively. Race members 130, 132 are rigidly affixed to the housing of the remote wire driver 14 and define an annular channel 134 therebetween. A pair of radius grooves or races 136 and 138 are formed in opposed channel surfaces of the race members.

An annular flange 140, integrally formed on the perimeter of turret 128, is received within the channel 134. A plurality of ball-type bearings 142 are seated within holes 144, which holes are evenly spaced around the turret flange. Bearings 142 travel within races 136, 138 thereby permitting the smooth rotation of the turret 128 under the computer driven control of a stepper motor 146 attached thereto. As noted, computer rotation of the turret stepper motor requires enablement of the safety interlock relay R7.

Figure 10:
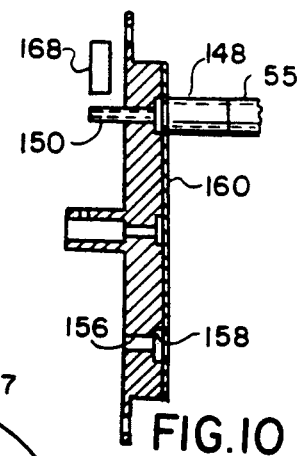
FIG. 10 is a sectional view taken along line 10—10 of FIG. 9 of the rotating turret further illustrating the placement of a catheter connector therein.
Figure 11:
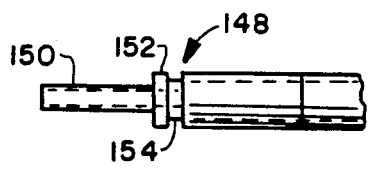
FIG. 11 is a side elevation view of a catheter connector.

Placement and locking of catheters 54 into the turret assembly 56 is best illustrated in FIGS. 8-13. As shown in FIG. 11, the end of each catheter is provided with a connector 148 defined, in part, by a cylindrical extension member 150, an annular locking flange 152 and a recess 154. A plurality of complementary catheter receptacle holes 156 are evenly spaced (FIG. 9) around a diameter of turret 128. Each hole includes a region of widened diameter 158 adapted to receive a catheter locking flange 152 therein.

Figure 12:
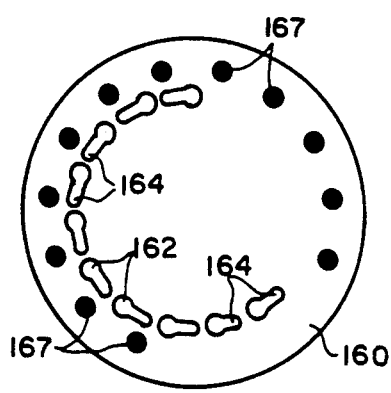
FIG. 12 is a rear elevation view of the turret assembly locking plate.

A circular catheter locking plate 160 is mounted adjacent the outside of the turret 128 for limited rotation with respect thereto. As shown in FIG. 12, the locking plate 160 is provided with a plurality of holes 162, with narrowed annular extensions 164, the holes having spacings corresponding to those of the catheter holes 156 in the turret. Thus, the locking plate may be rotated to admit passage and positioning of one or more catheters in the turret. Following catheter insertions, the locking plate 160 is rotated until the narrower annular extensions 164 are received within catheter connector recesses 154 thereby locking all catheters against inadvertent removal.

As previously noted, it is essential to establish the existence of a catheter in the active catheter position 55 as a prerequisite to wire extension, particularly extension of the active wire. Operation of the catheter-in-place system, which drives relays R9 and R15, is best shown by reference to the turret assembly FIGS. 8 and 14 and to the schematic diagram of FIG. 15.

Figure 14:
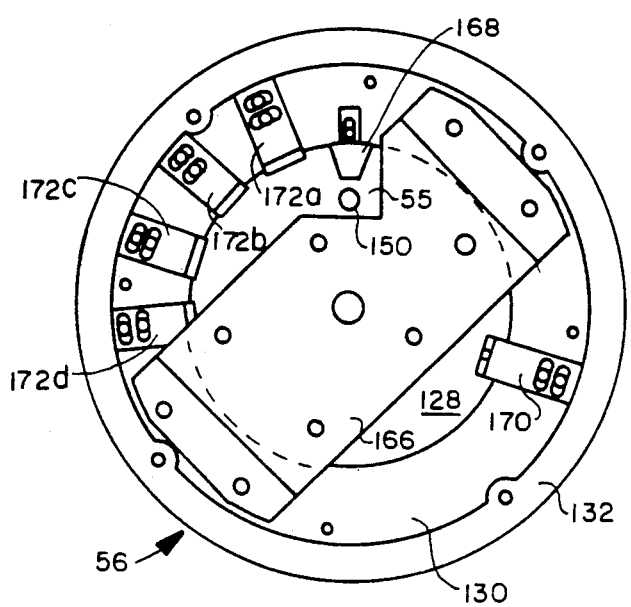
FIG. 14 is a rear elevation view of the turret assembly showing the catheter-in-place, catheter-locked, and turret-position/aligned optical sensors.
Figure 15:
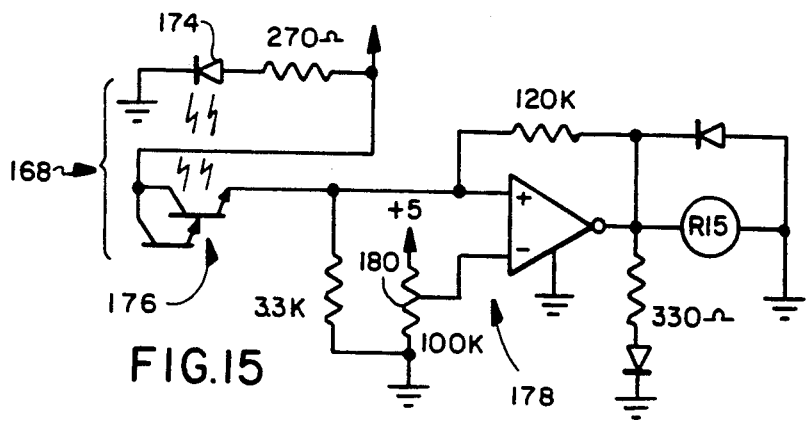
FIG. 15 is a schematic diagram of the catheter-in-place detection system.

FIG. 14 is a rear view of the turret assembly 56 showing the stepper motor 146 mounting bracket 166 and the proper orientation of the catheter-in-place optical sensor 168, the catheter-locked optical sensor 170, and the four turret-position/aligned optical sensor 172a-d.

The active catheter position is defined by the uppermost hole 156 of the turret 128, so long as that hole is properly aligned immediately above the turret/stepper motor axis. In this position, a wire extended from the output channel 83 (FIG. 3) directly enters the active catheter 55 mounted adjacent thereto.

FIGS. 10 and 14 illustrate the orientation of a catheter 54 in the active catheter position 55. The catheter-inplace sensor 168 is mounted to the fixed inner race 130, immediately above the active catheter position. It will be seen that the cylindrical tip member 150 of the catheter connector extends inwardly from the turret such that light from the optical sensor 168 will be reflected and returned thereto.

Referring to FIG. 15, the optical sensor 168 includes a light emitting diode (LED) 174 and a phototransistor pair 176. When a catheter is properly positioned in the active catheter receptacle, light from the diode 174 is reflected by the catheter tip member 150 and thereafter detected by phototransistor pair 176. The detected signal is, in turn, buffered by an operational amplifier comparator/buffer 178 thereby energizing relays R15 and R9. A potentiometer 180 is provided to set the light detection threshold at which the relay R15 will be energized. This same comparator/buffer circuit is used to interface each of the remaining optical sensors, including sensors 170, 172a-d, 190, and 192-195 (FIG. 3).

The catheter-locked optical sensor 170 (FIG. 14) is mounted to the inner turret race 130 such that the light therefrom is focused onto the rear face of the locking plate 160 through one of the holes 165 spaced around a circumference of turret 148. Each hole 165 is positioned to admit sensor light when the turret is aligned at one of its valid catheter positions. Referring to FIG. 12, a plurality of non-reflective paint dots 167 are provided on the rear face of the turret locking plate 160, one dot for each catheter position. More specifically, the rotation of the plate 160 into its catheter-locked position causes the corresponding rotation of the paint dots 167. When locked, one of the dots will be aligned such that the light from sensor 170 will not be reflected. Light reflection indicates the absence of a proper catheter-locked condition.

The structure and operation of the turret indexed and aligned system is best shown by reference to FIGS. 9, 14, and 15. The four turret-position/alignment optical sensors 172a-d are affixed to the stationary inner turret race 130, spaced at adjacent 30 degree intervals thereon. More specifically, these sensors 172a-d are oriented such that the light from each of the diode portions thereof is focused onto the back side of the turret 128. As the metallic turret is reflective, light from these diodes is ordinarily reflected back to the respective photodetectors.

A series of small non-reflective paint dots 182 (FIG. 9) are, however, positioned around an appropriate circumference of the turret thereby inhibiting light reflection to a sensor 172a-d whenever a dot is aligned adjacent that sensor. The dots 182 form a predetermined pattern or code uniquely identifying each of the ten valid turret/catheter positions. As will become apparent below, the only requirement for the paint dot code, other than the aforementioned uniqueness requirement, is that each valid 4-bit code must be comprised of at least one bit defined by the presence of a non-reflective dot.

As shown in FIG. 16, each of the four optical sensors 172a-d is buffered by a comparator/buffer 184a-d, of the type previously described. The four turret position outputs from these buffers are multiplexed, through buffer/latches 208 and 212 (FIG. 17), onto the bi-directional computer control and data bus 20 thereby permitting the computer 22 to monitor turret position.

The four buffer 184 outputs are additionally routed to a logical "OR" circuit 186 which, in turn, activates turret-aligned relays R13 and R14 upon the detection of at least one data bit corresponding to the non-reflection of light at optical sensors 172a-d. It will be appreciated that a possibility exists for turret misalignment, that is, for the turret to be lodged at some in-between position whereby none of the catheters would be properly oriented in the active catheter position 55 to receive a wire from the output 83.

Due to the fact that each of the non-reflective paint dots 182 is of small cross-section, reflected light will be detected by all sensors 172a-d unless the turret is aligned substantially correctly, that is, with at least one of the small dots adjacent an optical sensor. Any significant rotation of the turret from a valid orientation causes all of the dots to correspondingly rotate which, in turn, results in light being reflected at all sensor locations. It is for this reason—to distinguish between valid turret position codes and invalid turret alignments—that each valid turret/catheter position code must contain at least one non-reflective bit.

The preceding discussion has in large measure focused on the remote wire driver equipment 14 and, more specifically, on its unique structure for propelling, guiding, and storing ultra-thin delivery wires. Further, the preceding has addressed the cross-check and interlock and emergency failsafe retraction systems of the present invention which operate largely without computer intervention, to minimize the risk of system damage or loss of active wire control caused by computer malfunction, and to retraction the active wire, again without computer assistance, in the event of computer or other failure.

While the foregoing represent significant attributes of the present afterloader, necessary for proper and safe operation thereof, it should be understood that under normal operating conditions, it is the computer-based system that controls actual movement of the wires and turret and provides a further and sophisticated system of wire position control and emergency problem detection.

As previously discussed, the present arrangement provides a superior system for active wire retraction, virtually guarantying its retraction under a variety of adverse emergency conditions and, importantly, assuring that over-retraction cannot occur. However, full active wire retraction cannot be assured by the mere engagement of the active wire with the obstructed channel end 70, with park switch 72 located therein. Severance of the active wire could result in park switch activation, upon normal or emergency retraction, without the dangerous radioactive tip region of the wire being stowed properly within the safe 58.

Computer confirmation of full stowage of both the active and dummy wires is performed by analyzing the signals from selected optical sensors mounted along the wire channels 66, 67, and 83. These optical sensors are photodiode/detector pairs of the type previously described and function to detect the presence and absence of a wire in the selected channel locations.

Referring to FIG. 3, a home optical sensor 190 is positioned in the output channel 83, common to both wires, generally adjacent the turret assembly 56. Length optical sensors 192 and 193 are positioned near the respective terminal ends 72, 73 of the wire channels 66, 67. More specifically, each sensor 192 and 193 is spaced such that the wire path length between the respective sensor 192, 193 and the common home sensor 190 is approximately two millimeters shorter than the length of the corresponding wire. For example, with an active wire of 2100 millimeters, the home and active wire length sensors 190, 192 have a path length spacing of 2098 millimeters.

It will be appreciated that the mere checking of the home optical sensor 190 does not assure full wire retraction. A "home" signal will result upon the retraction of whatever portion of the wire remains intact. Without regard to the fact that the severed tip region, including the dangerous radioactive source, remains unstowed somewhere in the catheter. In short, the end of a broken or shortened wire will trigger the home sensor 190 in the same manner as that of a full length wire.

The present computer, therefore checks wire length upon each wire extension and retraction. This is accomplished by verifying that both optical sensors, home sensor 190 and path length sensor 192 or 193, simultaneously detect the presence of the delivery wire. A length measurement failure terminates the procedure, causes retraction of the wire, and sounds an alarm. If the active wire has broken, attending personnel must quickly locate the radioactive element and return it to an emergency backup lead safe (not shown).

Two overtravel sensors provide an additional level of protection and redundancy to the system. These sensors 194 and 195 are mounted along respective active and dummy wire channels 66,67 immediately below the wire drive systems 84 and 86. The computer control system is preprogrammed to accept a maximum treatment profile well below the 2100 mm length of the active wire, e.g. 1500 mm, thereby assuring that some portion of the wire will always remain adjacent the respective overtravel sensor. Therefore, the detection of a "no wire" condition by either overtravel sensor 194,195 necessarily signifies system malfunction terminating treatment and mandating attention by treatment personnel.

A twenty-five conductor computer data and control bus 20 interconnects the computer console 10 and remote wire driver 14. With reference to FIG. 17, three of these conductors 196 are dedicated to the emergency retraction interlocks/buttons 18, 44, and 52 and reset switch 122 previously considered in connection with operation of the emergency retraction system and run safety relay R1.

Eight conductors define a unidirectional computer-to-driver address and control bus 198 while eight additional conductors define a bi-directional data bus 200 between the computer and the remote afterloader. Finally, four conductors form a bus 202 which continuously provides the computer with the output data from the active and dummy wire position encoders 238 and 240.

All data from the computer 22, whether on the address/control bus 198 or bi-directional data bus 200, is buffered in conventional buffer/latches 204, 206, for example a 74HCT373. As this type of latch has tri-state output capability, the same type latch is employed at 208 and 210 to alternately select turret and wire position data, respectively, and, during computer read cycles, to output the selected data onto the bi-directional bus 200 through the latch 212. Finally, another latch 214 of the above type stores data from the computer during computer write cycles.

A 3-to-8 line decoder 216, for example a 74HC138, enables one of the position data latches 208 or 210 simultaneously with the enablement of the tristate output of the latch 212. Enablement of these latches is commanded, over the address/control bus 198, by the computer approximately every two milliseconds. Between these read cycles, the computer writes to the remote afterloader 14 by disabling the tristate output of latch 212 thereby releasing the bi-directional data bus 200 for incoming computer data. At the same time, a second 3-to-8 line decoder 218 enables the latch 214 thereby capturing eight bits of incoming data from the computer.

The first bit of computer data is the previously mentioned periodic signal monitored by the watchdog timer 124. The computer toggles this data line whenever the computer determines that everything is properly operating. In the continued absence of this toggling signal, e.g. for 0.6 seconds, the timer 124 actuates the relay R8.

Three data bits from the computer are dedicated to the respective active wire, dummy wire, and turret computer select functions. As discussed with reference to FIG. 7, the computer selects which stepper motor it intends to move by enabling the appropriate relay R10, R11, or R12.

The final four data bits are the actual stepper motor control signals which effect forward and reverse movement of the selected stepper motor. Referring to FIG. 18, each of the four stepper motor data bits, as updated by the computer and stored in the buffer/latch 214 approximately every 2 milliseconds, drives an operational amplifier stepper motor driver 220a-d. Each stepper motor driver includes an operational amplifier buffer 222, e.g. an LM324, which, in turn, is connected to the gate input of a MOSFET switch 224, e.g. an International Rectifier type Z22. Drivers 220a-d translate the 5 volt logic signals from latch 214 to switched 0 or 12 volt power signals 226a-d required by the stepper motors. The four stepper motor signals, on lines 226a-d are switched to the appropriate stepper motor by the previously considered stepper motor enabling relays R5, R6, and R7 (FIG. 7).

The following Table A represents the stepper motor truth table for rotation of the stepper motor in a predetermined first direction:

TABLE A

| A | B |
|---|---|
| $\overline{A}$ | $\overline{B}$ |
| $\overline{A}$ | B |
| A | B |

Similarly, Table B represents the stepper motor truth table for rotation of the stepper motor in the opposite direction:

TABLE B

| $\overline{A}$ | B |
|---|---|
| $\overline{A}$ | $\overline{B}$ |
| A | $\overline{B}$ |
| A | B |

Successive truth table rows represent successive computer stepper motor commands. It will be noted that the stepper motor control signals $\overline{A}$ and $\overline{B}$ are complements of respective control signals A and B. Thus, the first row of both truth tables indicates that FET outputs A and B, at control lines 226a and 226c, are switched "on", i.e. are grounded, while the other two control lines $\overline{A}$ and $\overline{B}$, 226b and 226d, are switched off, or floating at the 12 volt potential.

Referring to Table A, rotation commences upon receipt of the next computer instruction in which the polarities of lines B and $\overline{B}$ are reversed. Line B, 226d, is now grounded while line B, 226c, floats. In the same manner, the next command reverses the polarities of lines A and $\overline{A}$, and so forth until the wire or turret has been moved to the required position. As shown by Table B, stepper motor rotation in the opposite direction merely requires altering the switching sequence of the respective A, $\overline{A}$ and B, $\overline{B}$ inputs.

Stepper motors provide, as is well known, precise and predetermined angular displacements in response to each step command. The present stepper motors are of the four coil, 23 frame variety, for example, the turret motor is a Model K-82821-P1 manufactured by AirPax (Howard Industries). These motors exhibit 1.5 degrees angular rotation per step. The active and dummy drive motors 228 and 230 are Model 4SH-06A56S also manufactured by AirPax. These motors exhibit 1.8 degrees of angular rotation per step.

Thus, sixteen sequential step commands are required by the turret stepper motor 146 in order to select the next adjacent turret catheter position. Proper operation of the turret stepper motor is confirmed by the previously described turret-aligned cross-check and interlock system (FIGS. 7 and 16).

The 1.8 degree angular steps of the active and dummy stepper motors 228 and 230 are converted to linear wire movements by the capstans of the respective wire drive system 84,86. The diameter of each capstan 94, including rubber sleeves 92 (FIG. 6), is selected to achieve a predetermined lineal movement per motor step. In the present case, the wires move approximately 0.15 millimeters per step.

Equally importantly, the precise relationship between motor steps and active and dummy wire encoder 238,240 must be known. As explained in more detail below, computer oversight of proper wire movement is predicated on comparing the actual wire movements, as determined by reading wire position encoder 238,240 outputs against the calculated wire positions based upon the known number of commanded motor steps.

As shown in FIG. 17, a dedicated four line bus 202 continuously provides the computer 22 with active and dummy wire encoder 238,240 output information. Encoders 238,240 may be of the type manufactured by the Sony Corporation, Model RE10-256.

Figure 19A:
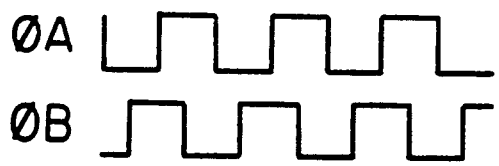
FIGS. 19a and 19b illustrate the output signal waveforms from the active and dummy wire encoders for rotation of the encoders in opposed first and second directions, respectively.
Figure 19B:
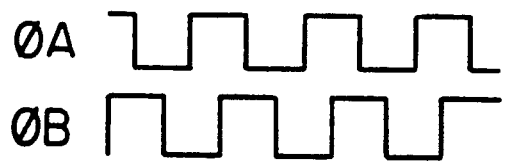

These encoders provide two-phased outputs as illustrated in FIGS. 19a,b. Both phases, designated as ∅A and ∅B, output signal pulses or "ticks" at the rate of 256 per shaft revolution. The direction of rotation is determined by the relative phase relationship between the respective A and B phases. Thus, in FIG. 19a, phase A leads phase B by 90 degrees. This corresponds to rotation of the encoder in one direction. In FIG. 19b, by contrast, phase A lags phase B by 90 degrees and, therefore, the encoder of FIG. 19b is rotating in the opposite direction to that of FIG. 19a.

Figure 20:
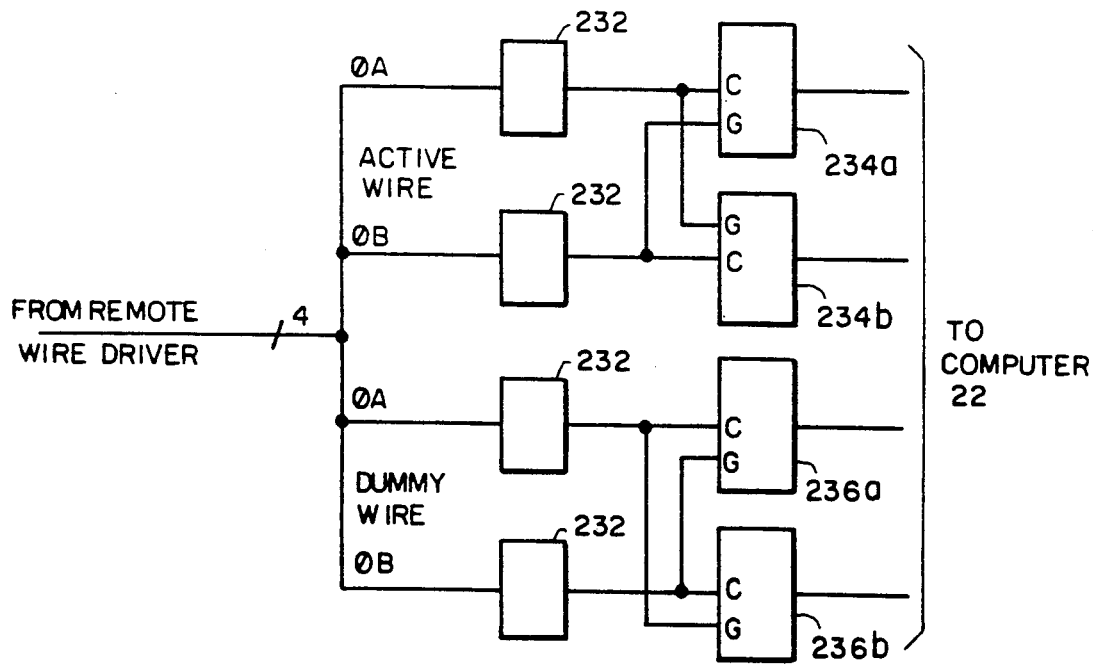
FIG. 20 is a block representation of the wire position encoders decoding counter logic located in the computer console; and, FIGS. 21a and 21b form a flowchart depicting console computer operation of the remote afterloader system of the present invention.

Referring to FIG. 20, the four encoder phase signals from the bus 20 are connected to opto-isolators 232, then, to four down-counters 234a,b and 236a,b, for example an Intel 8253. Counters 234a,b and 236a,b have clock C inputs for decrementing the respective counters and gate G inputs for inhibiting counter clocking. The four encoder phase outputs, from isolators 232, are connected to the clock C inputs of counters 234a,b and 236a,b. Additionally, the gate input G for each encoder phase counter is interconnected to the clock input C of the corresponding opposite phase output. Thus, the active wire encoder ∅A phase is connected to the clock input C of counter 234a and to the gate input G of counter 234b, while phase ∅B of the active wire encoder is connected to the clock input C of counter 234b and to the gate input G of counter 234a.

The above described gate/clock cross-coupling results in each counter operating only during rotation of the respective encoder 238,240 in one direction. For instance, extension of the active wire results in decrementing of counter 234a, only. Counter 234b is inhibited. Similarly, retraction of the active wire results in the decrementing of counter 234b, while counter 234a is inhibited.

In the present system, a 4 millimeter diameter encoder capstan 104 has been selected which results in approximately 20.37 output pulses per millimeter of wire travel. More significantly, each stepper motor step results, on average, in 3.03 encoder output pulses. This is the number that the computer uses to verify proper wire movement.

Figure 21A:
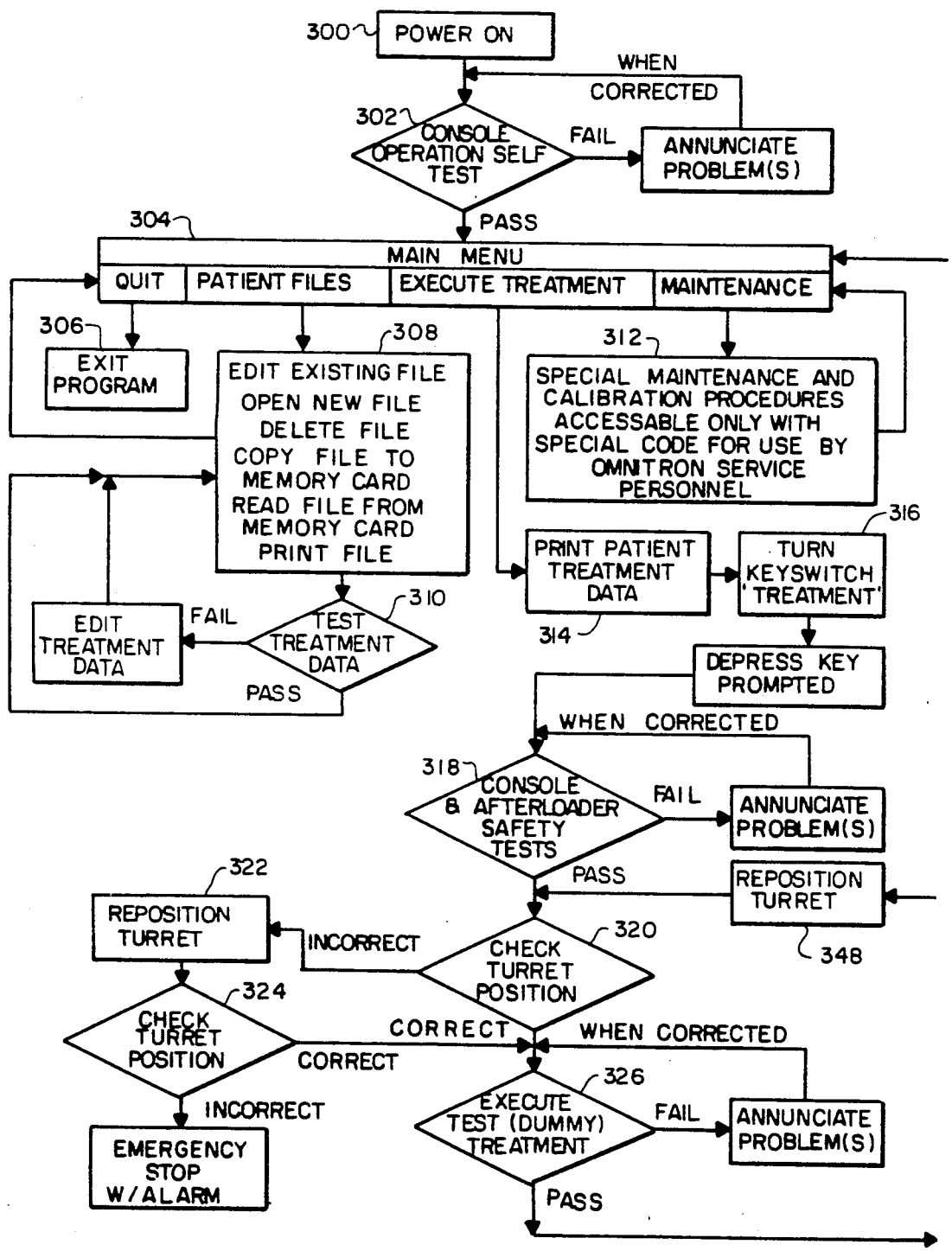
Figure 21B:
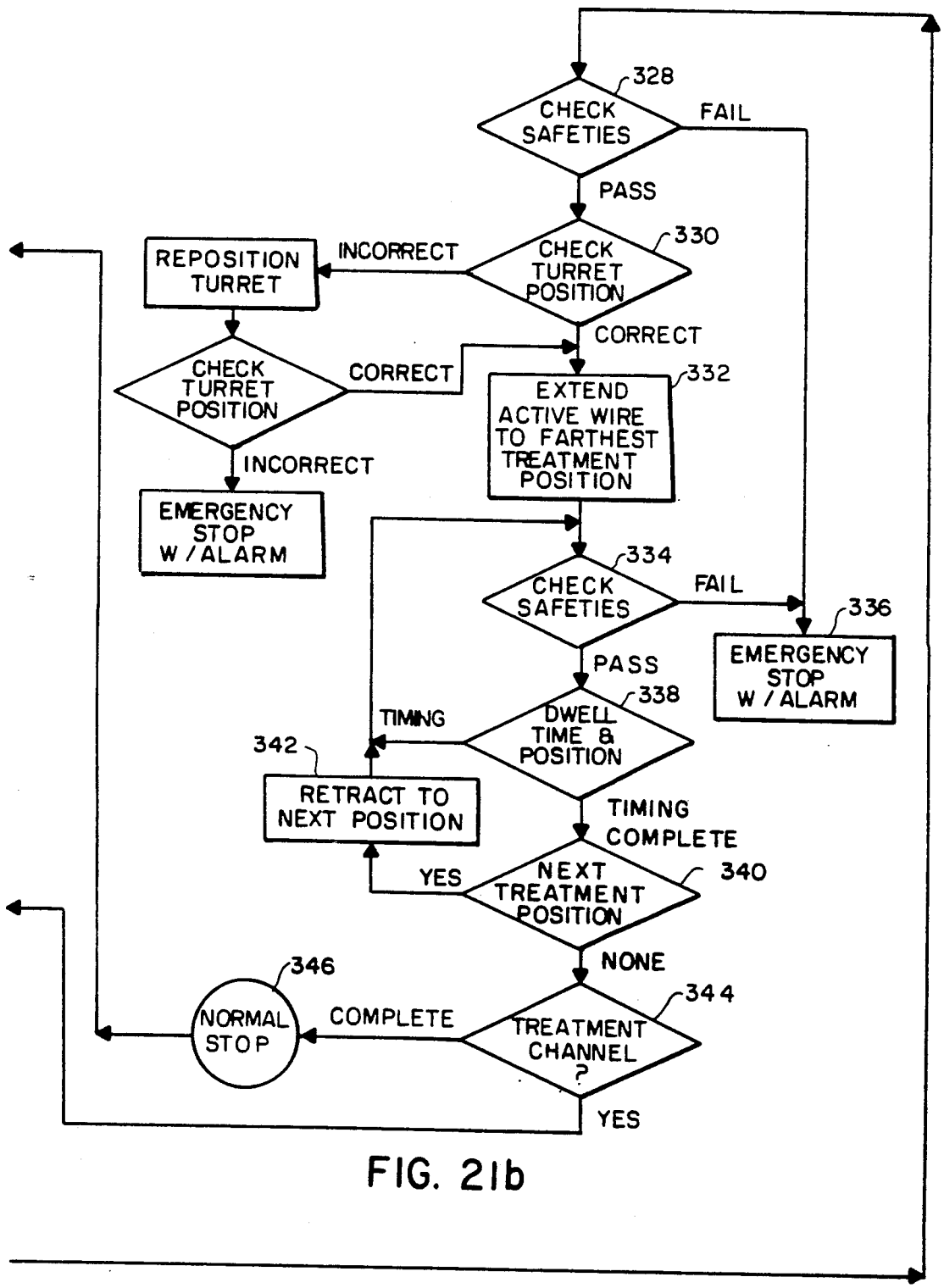

FIGS. 21a and 21b illustrate overall computer controlled operation of the present remote wire afterloader system. Upon system power-up 300 and initial console self-test 302, a main menu 304 permits optional courses of action including exiting the program 306 thereby permitting use of computer 22 for other tasks.

Patient treatment information, including the proposed treatment profile, must be entered 308. Such profiles typically include a listing of each treatment position, by distance measure from the turret reference point, as well as the treatment or dwell time at each such position.

This information is checked 310 to verify, for example, that the selected profile does not violate system or medically based operational rules. Specifically, in its present and preferred arrangement, profile parameters must not include treatment positions exceeding 1500 millimeters or position dwell times exceeding 60 seconds. Further, the dwell positions must be arranged in descending order and not be closer together than a predetermined distance as specified during system initialization, i.e., at 312.

The requirement for descending order dwell positions is extremely important to proper operation of the present afterloader particularly in view of the extremely fine diameter wire for which the present system is intended to operate. Notwithstanding the dummy wire pretesting of each catheter to verify that an ultra-thin wire can be moved to the requisite dwell positions, there always remains some possibility that an ultra-thin wire will become jammed precluding further inward movement.

On the other hand, once a wire has been inserted to its maximum insertion position, the likelihood of jamming upon the retraction of that wire is extremely small. Therefore, it is preferable to commense treatment at the maximum dwell position whereby the active wire may immediately be retracted should the computer detect undue wire slippage at the drive capstan. This condition, as noted, corresponds to encoder 238,240 output pulses falling below the expected 3.03 pulses/motor step.

A maintenance capability 312 is accessible to qualified personnel for the purpose of source loading, unloading, calibration, and the setting of treatment profile parameter limits such as maximum dwell time and minimum dwell step sizes.

A patient treatment record, including proposed treatment profile, is printed 314 prior to each treatment session. Actual initiation of a treatment session requires actuation of a key switch 316 by the doctor or other personnel having appropriate authority.

Prior to initiating the treatment profile, the computer performs, in essence, a back-up check of the previously described non-computer cross-check and interlock safety system. Specifically, the computer verifies at 318 that the treatment room door is closed; that the console-to-remote driver communications bus 20 is functioning; that both active and dummy wires are parked; that the wire position sensors are functioning; and, that the emergency backup battery voltage is proper.

Next, the turret position is checked at 320 by verifying that the unique four bit turret position code corresponds to that of the desired turret position. The turret is repositioned at 322 and rechecked at 324 if the initial position is not correct.

The system is now ready to test the first catheter position by cycling the dummy wire at 326. The computer selects the dummy wire by latching the appropriate control code at latch 214 thereby energizing the relay R11 (FIGS. 7 and 17), thereafter, outputting a series of stepper motor commands sufficient to move the dummy wire 10 millimeters beyond the longest programmed dwell location for the catheter under test. The wire is moved slightly beyond the furthest programmed dwell position, and then fully retracted.

More specifically, the computer first calculates the number of steps required to extend the wire to the desired maximum position (including the 10 millimeter overextension) and the corresponding number of pulses expected from the dummy wire encoder. These calculations are based on a reference point defined by the home optical sensor 190, located adjacent the turret.

The computer commences movement of the dummy wire until the forward end thereof triggers sensor 190. The computer then presets the dummy counters 236a,b (FIG. 20) to their maximum value and rocks the wire one step backward and one step forward to verify counter operation. In addition, the computer verifies that there is approximately a 2 millimeter overlap where both home sensor 190 and dummy length sensor 193 register the presence of the dummy wire. Failure to detect this overlap condition, or failure to register the presence of the wire at all times by at least one of the sensors, indicates that the wire has become separated.

Stepping of the dummy stepper motor now commences. Dummy wire movement is continued until the previously calculated target value of encoder 240 output pulses is reached. This number is reached when the difference in values of the forward and reverse counters, 236a and 236b, equals this number. This difference method of position determination is immune to accumulated positioning errors since the wire is moved to a precalculated value instead of incremental values.

During dummy wire extension, the computer is performing cross-checks to verify that no obstructions or jams have been encountered. First, wire jams are determined by comparing the number of encoder 240 pulses received per stepper motor step. As noted, 3.03 encoder pulses are expected for each step. If pulses stop, or fall below this rate, the wire is retracted and a jam condition is annunciated at the console.

The computer further checks the overall number of steps required to obtain the desired position of the wire. If the number of steps exceeds the calculated number by more than a predetermined limit, an obstruction is assumed. The wire is withdrawn and an appropriate alarm sounded.

The dummy wire is fully retracted to terminate the dummy wire test cycle 326. Upon retraction, the length of the dummy wire is again checked to confirm that the wire has not broken.

Prior to commencing extension of the active wire, the system safeties and turret position are again checked at 328 and 330. The active wire is then extended to the furthest treatment position at 332 defined by the current treatment profile. Extension of the active wire is substantially identical in all aspects to that of the previously described dummy wire. Thus, the length of the wire is checked prior to extension. The wire is then precisely positioned at the first treatment location by, as before, first over-extending the wire by 10 millimeters. The position of the active wire is monitored by computing the difference between the extension and retraction encoder pulse counters 234a and 234b. Wire jamming and obstruction tests are performed, again, as outlined with reference to extension of the dummy wire.

During the treatment phase, the computer continues to monitor system safety indices at 334 including the long term watchdog timer 126,R16. Since the active wire is fully retracted and parked between each catheter treatment profile, this timer reflects active wire extension beyond the maximum treatment profile allowed by the computer. In short, this timer flags a potentially hazardous condition necessitating emergency retraction at 336.

Upon completion of the preprogrammed dwell time for each active wire position at 338, the computer checks to see whether there are further treatment positions for that catheter at 340, if so, the active wire is retracted to the next adjacent dwell position at 342. As noted, the computer monitors active wire position by taking the difference between the extension and retraction counters 234a,b.

Following the last treatment or dwell position for each catheter, the active wire is fully retracted, checking the overall wire length to confirm that the entire wire length, including the active iridium tip portion, has been properly retrieved. The computer thereafter determines whether there are additional catheter treatment profiles to be run at 344. If not, a normal stop at 346 and return to the main menu at 304 occur.

If an additional catheter treatment profile ha been programmed, the turret is repositioned at 348 and that position checked at 320. Prior to running each active wire treatment profile, the new catheter position is checked by the dummy wire at 326 as previously described.

What is claimed is:

1. Apparatus for the remote handling of a radioactive source in the treatment of cancer, the source being formed on the end of a delivery wire, the remove handling apparatus comprising delivery means for delivering the radioactive source on the wire into a patient, control means positioned remotely from said delivery means for controlling said delivery means and bus means interconnecting said control means and said delivery means for transferring control and data signals therebetween, said delivery means including a shielded receptacle for storing the radioactive source, means for detecting malfunction of the remote handling apparatus, and means responsive to detection of said malfunction for automatically retracting the radioactive source on the wire into said shielded receptacle to remove the radioactive source from the patient and safely return it to said shielded receptacle in the event of said malfunc-

21 tion, said means for automatically retracting including a non-stepper dc motor, a capstan driven by said motor, a pinch roller for cooperating with the capstan to retract said wire, a pinch roller for cooperating with the capstan to retract said wire, a pinch roller solenoid which when energized pulls said pinch roller away from said capstan, and biasing means for urging said pinch roller toward said capstan when said solenoid is de-energized 2. Cancer treatment apparatus for the remote handling of a radioactive source formed on a source end of a delivery wire, the treatment apparatus comprising:
wire moving means for moving said delivery wire to insert the source end thereof into a patient;
movement sensing means, remote from said wire moving means, for generating movement signals representing the movement of said wire; and
control means positioned remotely from said wire moving means and said movement sensing means for controlling the movement of said delivery wire by said moving means, said control means being responsive to said movement signals for controlling said wire moving means to accurately move said source end of said wire a first predetermined distance into said patient.

3. The cancer treatment apparatus of claim 2 comprising timing means for indicating the passage of time after the movement of said delivery wire; and
said control means comprises means responsive to said timing means and said movement signals for controlling said wire moving means to move said delivery wire and position said source end a second predetermined distance into said patient.

4. The cancer treatment apparatus of claim 3 comprising means responsive to said timing means for retracting said source end of said delivery wire into a radiation shield means.

5. The apparatus of claim 2 wherein said wire moving means comprises a rotatable drive capstan, pinch roller means for urging said wire into frictional engagement with said drive capstan so that rotation of said drive capstan is translated into linear movement force in said wire, and means for rotating said drive capstan.

6. The apparatus of claim 5 wherein said motion sensor comprises a wire motion sensor capstan in frictional engagement with said delivery wire so that linear movement of said wire is translated into rotational movement of said motion sensor capstan, and a rotation detection means for measuring the rotation of said motion sensor capstan.

7. Apparatus for moving a radioactive source formed at the end of a delivery wire into and out of a guide tube connected to a patient for treatment of said patient, said apparatus comprising:
a rotatable capstan;
guide means for positioning said delivery wire in close proximity to said capstan, said delivery wire being relatively straight at said capstan and running parallel to the plane of rotation of said capstan;
a bi-directional motor coupled to said capstan for the rotation thereof;
a moveable pinch roller for selectively urging said wire into frictional engagement with said capstan so that rotation of said capstan is translated into linear movement force in said delivery wire; and
control means responsive to requests for the movement of said wire for driving said moveable pinch roller to urge said wire into frictional engagement with said capstan and for energizing said motor.

22

8. The apparatus of claim 7 comprising a wire retraction motor and means responsive to a failure condition for energizing said wire retraction motor to withdraw said source from said guide tube.

9. The apparatus of claim 8 comprising means for de-energizing said wire retraction motor when said source is completely withdrawn from said guide tube into radiation safe storage in said apparatus.

10. The apparatus of claim 7 comprising:
movement sensing means independent of said bi-directional motor and said capstan for sensing the movement of said delivery wire within said guide tube; and
said control means comprises means responsive to said motion sensing means for controlling the position of said source within said guide tube.

11. The apparatus of claim 10 wherein said movement sensing means comprises:
an encode means, having a rotatable shaft, for generating signals representing the rotation of said shaft;
means for frictionally engaging said delivery wire and said rotatable shaft such that the movement of said delivery wire rotates said rotatable shaft; and
means for conveying said signals representing the rotation of said shaft from said encode means to said control means.

12. Apparatus for moving a radioactive source formed at the end of a delivery wire into and out of a guide tube connected to a patient for the treatment of said patient, said apparatus comprising:
program controlled control unit for controlling the treatment of said patient by said radioactive source and, while properly controlling said treatment, for generating periodic timer signals;
a control unit check timer, independent of said control unit, for generating treatment terminate signals at predetermined intervals;
means responsive to each of said periodic timer signals for inhibiting the generation of one of said treatment terminate signals; and
means responsive to said treatment terminate signals for overriding treatment control by said control unit and for retracting said source from said guide tube.

13. The apparatus of claim 12 wherein said check timer comprises means for generating treatment terminate signals said predetermined interval of time after being reset and said inhibit means comprises means responsive to each periodic timer signal for resetting said check timer.

14. The apparatus of claim 13 wherein the predetermined interval of said check timer is less than 1 second.

15. Apparatus for moving a radioactive source formed at the end of a delivery wire into and out of a guide tube connected to a patient for the treatment of said patient, said apparatus comprising:
control means for generating wire movement control signals to control the insertion of said source wire into said guide tube;
wire movement means responsive to said wire movement control signals for extending said source wire into said patient via said guide tube;
means for generating a retraction signal when said source wire has been extended into said patient for a predetermined period of time, said predetermined period of time being the maximum time that said source is to be extended into said patient; and retraction means responsive to said retraction signal for terminating said movement of said wire by said wire movement means, and for retracting said wire into said apparatus.

16. Apparatus for moving a radioactive source formed at the end of a delivery wire into and out of a guide tube connected to a patient for the treatment of said patient, said apparatus comprising:
a first power source;
a second power source;
wire movement means for extending said source wire into said guide tube when energized by power from said first power source;
wire retraction means for retracting said wire from said patient when energized by power from said second power source;
protection circuitry having a first state when energized by said first power source, and a second state when said first power source energization is withdrawn, said protection circuit in said first state for connecting power from said first power source to said wire movement means and in said second state for removing the connection of power from said wire movement means and for connecting power from said second power source to said wire retraction means;
means for energizing said protection circuitry from said first power source; and
means responsive to fault conditions in the operation of said wire movement means for de-energizing said protection circuitry.

17. The apparatus of claim 16 wherein said second power source comprises a rechargeable storage battery.

18. The apparatus of claim 16 wherein said protection circuit comprises a relay having an actuating coil selectively energizible from said first power supply.

19. The apparatus of claim 16 comprising:
computer controlled means for controlling said wire movement means;
means for generating a computer fault signal in response to faulty operation by said computer controlled means; and
said means for de-energizing said protection circuitry comprises means responsive to said computer fault signal for de-energizing said relay.

20. The apparatus of claim 19 wherein said computer fault signal generating means comprises a timer resettable by said computer control means during non-faulty operation of said computer controlled means.

21. The apparatus of claim 16 comprising:
means for generating treatment time limit fault signals when said wire has been extended into said guide tube for more than a predetermined maximum time; and
said means for de-energizing said protection circuitry comprises means responsive to said treatment time limit fault signals for de-energizing said protection circuitry.

* * * * *

UNITED STATES PATENT AND TRADEMARK OFFICE
CERTIFICATE OF CORRECTION

PATENT NO. : 5,103,395
DATED : April 7, 1992
INVENTOR(S) : David W. Spako et al.

It is certified that error appears in the above-identified patent and that said Letters Patent is hereby corrected as shown below:

On the title page, for the primary examiner, change "Gary" to "Gail".

At Column 7, line 37, change "annunciator" to --annunciators--.
At Column 12, line 3, change "R!5" to --R15--.
At Column 13, line 33, change "!70" to --170--.
At Column 20, line 45, change "ha" to --has--.
At Column 20, line 54, change "remove" to --remote--.
At Column 21, line 52, after "for" insert --the--.

Signed and Sealed this

Twentieth Day of July, 1993

*Attest:*

MICHAEL K. KIRK

*Attesting Officer*     *Acting Commissioner of Patents and Trademarks*